United States Patent [19]

Muller

[11] Patent Number: 4,624,868
[45] Date of Patent: Nov. 25, 1986

[54] BORATED POLYSACCHARIDE ABSORBENTS AND ABSORBENT PRODUCTS

[75] Inventor: Ernest G. Muller, Highland Park, N.J.

[73] Assignee: Colgate-Palmolive Company, New York, N.Y.

[21] Appl. No.: 781,187

[22] Filed: Sep. 25, 1985

Related U.S. Application Data

[60] Continuation of Ser. No. 421,658, Sep. 22, 1982, abandoned, which is a continuation of Ser. No. 275,479, Jun. 19, 1981, abandoned, which is a division of Ser. No. 104,204, Dec. 17, 1979, Pat. No. 4,333,461.

[51] Int. Cl.$^4$ .................... A61F 13/16; A61F 13/18; A61F 13/20; B05D 3/02
[52] U.S. Cl. ......................................... 427/384; 34/5; 106/205; 427/398.4; 428/308.4; 428/497; 604/369
[58] Field of Search ................... 34/5; 106/129, 205; 128/284, 287; 426/384, 385; 427/384, 398.4; 428/311, 497, 498, 308.4; 604/369

[56] References Cited

U.S. PATENT DOCUMENTS

| | | | |
|---|---|---|---|
| 3,070,095 | 12/1962 | Torr | 604/364 X |
| 3,215,634 | 11/1965 | Walker | 252/311 |
| 3,702,779 | 11/1972 | Fadner et al. | 34/5 X |
| 3,903,889 | 9/1975 | Torr | 128/287 |
| 4,055,180 | 10/1977 | Karami | 128/287 |
| 4,096,283 | 6/1978 | Rahman | 426/385 X |

FOREIGN PATENT DOCUMENTS

769236  3/1957  United Kingdom ............... 106/205

Primary Examiner—Michael R. Lusignan
Attorney, Agent, or Firm—Herbert S. Sylvester; Murray M. Grill; Norman Blumenkopf

[57] ABSTRACT

Guar gum as an exemplification of cis-1,2-diol polysaccharides is first hydrated then thickened by cross-linking with borax and finally dried to powder to flake form, preferably by freeze drying. The resulting particles can absorb up to 100 times their weight or more of aqueous fluids such as urine. Absorbent articles, such as disposable diapers, bandages, and the like are formed with the borax-cross-linked guar gum as absorbent. In a preferred diaper the dry absorbent particles of the borax cross-linked guar gum are placed in the cells of a cellular or bubble-type substrate.

9 Claims, No Drawings

BORATED POLYSACCHARIDE ABSORBENTS AND ABSORBENT PRODUCTS

This application is a continuation of application Ser. No. 421,658, filed Sept. 22, 1982, now abandoned, which is a continuation of Ser. No. 275,479, filed June 19, 1981, now abandoned, which is a division of Ser. No. 104,204, filed Dec. 17, 1979, now U.S. Pat. No. 4,333,461, patented June 8, 1982.

This invention relates to super absorbent materials, a process for preparing these materials and absorbent articles such as diapers containing the super absorbent. More particularly the present invention relates to borax cross-linked cis-1,2-diol polysaccharides super absorbents, the method of parparing the super absorbent borax cross-linked polysaccharides and absorbent articles such as diapers containing the dry super absorbent material, and especially as exemplified by guar gum.

Many attempts have been described in the patent literature to prepare super absorbent materials, i.e. materials which are capable of absorbing many times their weight of water or various body fluids.

The following list is representative of United States patents which have issued in this area: U.S. Pat. No. 3,528,421 to Vicen L. Valliancourt, et al (disposable absorbent underpad for hospital patients or similar product, hydrous calcium silicate chemical absorbent); U.S. Pat. No. 3,563,243 to Julius A. Lindquist (absorbent pads such as diapers, underpads and the like- hydrophilic polymer absorbent); U.S. Pat. No. 3,669,103 to Billy Jean Harper, et al. (absorbent products containing a hydrocolloidal polymeric absorbent lightly cross-linked polymer such as poly-N-vinyl-pyrrolidone, polyvinyltoluenesulfonate, poly-sulfoethyl acrylate, and others); U.S. Pat. No. 3,686,024 to Rober J. Nankee (water absorbent articles coated with a water-swollen gel such as cross-linked partially hydrolized polyacrylamide); U.S. Pat. No. 3,670,731 to Carlyle Harmon (absorbent dressing using water soluble hydrocolloidal composition); U.S. Pat. No. 3,783,872 to Paul A. King (absorbent articles such as diapers, and the like using insoluble hydrogels as the absorbing media); U.S. Pat. No. 3,898,143 to Per Gunnar Assarsson, et al. (disposable absorbent articles using poly(ethylene oxide) and at least one other water soluble polymer co-cross-linked by high energy irradiation); U.S. Pat. No. 4,055,184 to Hamzeh Karami (absorbent pads for disposable diapers, sanitary napkins, bandages or the like using solid, finely-divided mixture of a hydrolized starch polyacrylonitrile graft copolymer in acidic form and a non-irritating and non-toxic water-soluble basic material); U.S. Pat. No. 4,069,177 (water absorbing and urine stable step-wise grafted starch-polyacrylonitrile copolymers); U.S. Pat. No. 4,076,663 to Fusayoshi Masuda, et al. (water absorbing starch resins); U.S. Pat. No. 4,084,591 to Toshio Takebe, et al. (absorber for blood made from filaments of a lower alkyl or a lower hydroxyalkyl substituted cellulose ether).

However, particularly with respect to their application for absorbing or holding body fluids such as in diapers, sanitary napkins, bandages, gloves, sporting goods and the like the absorbent materials and absorbent products described in these patents have not been commercially acceptable. Such problems as insufficient absorbing capacity, breakdown of the gel structure upon contact with saline fluids, incompatibility with absorbent articles, still exist.

In U.S. Pat. No. 3,903,889 to David Torr the patentee describes as an absorbent composition for use in absorbent products a guar gum which is modified with borate anion in an amount sufficient to complex the gel formed from the hydration of guar gum alone. Specifically, the patentee teaches introducing borate ion into the absorbent product in the form of an essentially water insoluble borate-release agent in which the free borate ion is released slowly to the absorbent system and only after the aqueous liquid sought to be absorbed by the product has entered the product itself. It is suggested that the modified guar gum can absorb up to at least 20 times its weight of water to produce a relatively dry non-sticky and inert gel.

It has been found, however, that most of the aforementioned materials except those made from guar gums are highly sensitive to salts and are subject to breakdown in the presence of salts including sodium and potassium salts, e.g. NaCl. Still further, the described absorbing capacity of the borate modified guar gums of Torr have been found to be insufficient and the absorption-gellation rate is too slow for practical applications, especially in a disposable diaper.

It has now been found in accordance with the present invention that it is possible to use as the absorbent material in absorbent products particles of dried borax cross-linked guar gum (as illustrative of the class of cis-1,2-diol polysaccharides) which have been formed prior to incorporation into the absorbent product. This is in contrast to the technique disclosed by Torr wherein the borax cross-linked guar gum is formed in situ in the absorbent product and only after the liquid to be absorbed has penetrated into the absorbent product.

In accordance with the present invention a novel form of dry particles of borox cross-linked guar gum is obtained by mixing guar gum and water for a time sufficient to allow the guar gum to become at least substantially completely hydrated; adding an aqueous solution of a source of borate ion to the hydrated guar gum to cross-link the guar gum and form a thickened mass; and heating the thickened mass to drive off water contained therein. The dry cross-linked guar gum can then be reduced to flake form or alternatively to a very finely powdered form so that formation of a shell barrier, a phenomenon referred to in the Torr patent, does not become a significant problem. Preferably the thickened mass is freeze-dried whereby the borax cross-linked guar gum is recovered as a dry porous material.

Thus, in one embodiment of the present invention guar gum is dispersed in an aqueous medium to obtain a viscous solution of hydrated guar gum; the viscous solution is mixed under high heat conditions until the solution is uniformly homogenized; borax or other borate releasing compound is added to the homogenized solution of hydrated guar gum while stirring the solution until the hydrated guar gum is cross-linked and forms a thickened gelled mass; the thickened mass is formed into a sheet; and the sheet is subjected to a freeze-drying process.

Accordingly, the present invention also provides absorbent borax cross-linked guar gum products which may be in various forms such as very fine powdery materials, flakes or porous freeze-dried particles and the absorbent articles containing these absorbent materials.

A preferred form of the absorbent article according to the present invention is a disposable diaper, the overall structure of which may be the same as in any conventional disposable diaper of the type including a body contacting top sheet which is liquid permeable, a liquid impervious bottom sheet and an intermediate absorbent layer of or containing the borax cross-linked guar gum absorbent material. With respect to specific constructions of the disposable diapers according to the present invention reference can be made in general to the patents listed above, the disclosures of which are incorporated herein by reference. A particularly preferred absorbent article structure is illustrated, for example, in U.S. Pat. No. 4,055,180 in which an absorbent pad has associated therewith a plurality of pockets or cells contained within the pockets. Other absorbent articles in which the absorbent materials of the present invention can be especially advantageously used, include, for example, sanitary napkins, bandages, sporting goods, gloves such as work gloves, cosmetic gloves and the like, all of which absorbent articles have in common that they are designed for throw-away single use applications and they are used in contact with body fluids such as urine, catamenial discharge, perspiration and the like. In its broadest sense, therefore, the present invention provides absorbent articles in which absorbent particles of the borax cross-linked guar gum are contained in, on, or carried by a substrate material, the articles being capable of being held in contact with the body of the user such that the absorbent particles are in contact with body fluids exuded by the body either directly or after passing through a body-contacting cover sheet.

The present invention will now be described in greater detail in connection with the following description and nonlimitating illustrative examples.

The guar gum starting material is a commercially available hydrocolloid polysaccharide material which is a species of galactomannan and which can be derived from the plant *cyamposis tetragonoloba*. Additionally, various modifications of guar gum which are well known in the art and are commercially available can also be used as the starting guar gum material. Suitable forms of the modified guar gum include the oxidized, acetylated, carboxylated, esterified, methylated, aminated, etherated, sulfated and phosphated derivatives of guar gum. A preferred starting form of modified guar gum is carboxy-methylated hydroxypropylated guar gum which is commercially available from Celanese (Stein-Hall) under the tradename Jaguar CMHP. A carboxymethyl modified guar gum or hydroxypropylated derivative of guar gum are also particularly advantageous forms of modified guar gum.

The guar gum (or modified guar gum) is mixed with sufficient water until the guar gum is completely hydrated. It has been found that guar gum which has not been hydrated will not cross-link with the borate ions. Desirably, deionized water is used. The temperature of the water is not particularly critical but generally water at room temperature to boiling, preferably from about 50° C. to boiling will be used for the hydration. The amount of water is also not critical and generally will range from about 20 grams to about 100 grams water per gram of guar gum or modified guar gum, preferably from about 30 ml to about 80 ml water per gram of guar gum or modified guar gum.

The water-guar gum solution is allowed to stand for a time sufficient until the guar gum or the modified guar gum is at least substantially completely hydrated preferably completely hydrated. Generally from about 5 minutes to about 2 hours will be sufficient for the guar gum to be completely hydrated. Amounts of guar gum to water ranging from about 0.5 grams to about 20 grams guar gum preferably from about 1 to about 10 grams per 100 ml water will produce a thickened, viscous and flowable solution.

In order to minimize the amount of energy required to remove the water from the subsequently formed borox cross-linked guar gum, the amount of water relative to the amount of guar gum should be kept as low as possible. Therefore, it is preferable to use the minimum amount of water to sufficiently hydrate the guar gum and allow the subsequent cross-linked reaction and gel formation to occur. However, if the amount of water is too low the completion of the hydration will be difficult to achieve and the hydrated mass may be too thick and viscous to effect the subsequent cross-linking reaction. Therefore, amounts of hydration water ranging from about 30ml to about 70 ml preferably from about 30 ml to about 50 ml. per gram of guar gum is the preferred range.

To assure complete hydration of the guar gum the guar gum can be added to the deionized water with vigorous stirring. Generally, the hydration reaction is relatively pH insensitive and hydration will occur at pH levels of about 2 to about 10 or higher. However, hydration occurs most rapidly at pH's in the range of from about 4 to about 8 and preferably at nearly neutral or slightly acidic pH levels.

After the hydration reaction is completed an aqueous solution preferably of as high a concentration as feasible containing a source of borate ions is added to the hydrated guar gum solution to cross-link the guar gum and obtain a thickened gel-like mass. The cross-linking reaction is believed to take place between the hydroxyl groups of the hydrated guar gum and the borate ions. The source of the borate ions can be any water soluble material which can contribute a borate ion to the cross-linking reaction. Suitable materials include the alkaline metal, alkaline earth metal and ammonium salts of borate anions. Useful borate anions include the tetraborate, metaborate and perborate anions. Borax ($Na_2B_4O_7 \cdot 10H_2O$) is the preferred source of the borate ions as the cross-linking agent. The concentration of borax (used as the measure of the concentration of the borate ions) in the aqueous solution is not particularly critical. Generally, the concentration of borax required to effect the cross-linking can be determined by routine experimentation or by calculation. For most purposes an aqueous solution containing from about 0.1 g to about 20 grams borax preferably 1 to 10 g is generally sufficient for each 100 grams guar gum of the hydrated guar gum viscous solution. Generally, the concentration of the borate ions should be selected to be in a slight stoichiometric excess to the number of cross-linkable hydroxyl groups and other reactive groups of the hydrated guar gum since slightly basic pH's will promote the subsequent absorption of body fluids which may themselves be slightly acidic. Other alkaline substances which do not interfere with the cross-linking reaction may also be added to the cross-linking reaction to give slightly alkaline pH to the cross-linked guar gum, for example pH 7.1 to 9.0. Examples of the alkaline substance includes sodium biocarbonate, sodium carbonate, alkali metal phosphates, and alkaline salts of organic acids, such as sodium or potassium salts of citric acid, tartaric acid, and the like. The aqueous solution containing the borate ions is quickly added to the hydrated guar gum with sufficient mixing to assure thorough homogenization. The temperature during the cross-linking reaction is not particularly critical but can generally range from about room temperature to about 100° C. preferably from about 35° C. to about 60° C. Accordingly, it is not necessary to heat the aqueous solution of the borate ions or to wait until the hydrated guar gum is cooled before adding the borate ion-containing solution to the hydrated guar gum.

The pH of the cross-linking reaction should be alkaline but otherwise not particularly critical and will proceed at pH's in the range of from about 7 to 11, preferably from about 7.5 to about 9.

The cross-linking reaction will generally be completed in from about 1 to about 24 hours depending upon such factors as the temperature, pH, amount, rate and degree of mixing, concentration of the borate ions and the like. The crosslinking reaction is completed when the viscosity of the resulting thickened gel-like mass no longer changes. Depending on the quantity of water used to hydrate the guar gum the viscosity of the borax cross-linked guar gum will range from about 50,000 centipoises to about 150,000 centipoises. Accordingly, the hydrated borax cross-linked guar gum may have a consistency ranging from a coherent slowly pourable gel through first stage gelling or gelation in which the thickened mass is no longer pourable but does not have dimensional stability and will spread if unconfined or second stage gelling in which the gel will have some dimensional stability and will temporarily hold a shape but will spread if unconfined for a short period of time.

The resulting thickened mass of the hydrated borax crosslinked guar gum is then dried by heating until the water content is reduced to about 0% to about 20%, more preferably from about 0% to about 15% water by weight of the dried product. The hydrated and cross-linked guar gum can be dried by any conventional drying technique including, for example, steam heat, air-drying, vacuum or micro-wave oven techniques or combination thereof. However, a particularly preferred and advantageous means for drying the gelled material is by freeze-drying.

For example, the gelled material may be dried by placing it on a drying drum using stem heat or similar apparatus. The dried material will be in the form of a brittle sheet or mass which will readily crumble by slight manual manipulation or by milling into powder or flake shaped particles. It is advantageous to shear the dried mass into the form of very thin flakes having generally thickness as of about 10 microns to about 200 microns, preferably from about 10 to about 50 microns and having an aspect ratio (ratio of length to thickness) of about 10:1 to about 50:1, preferably from about 30:1 to abou 50:1. In this form when the flakes are rehydrated when they come into contact with water, urine or other liquid substance the formation of a shell barrier, i.e. the formation of an impenetrable gel film on the exterior surface of the borax cross-linked guar gum absorbent particles which prevents migration of the fluid to be absorbed into the interior of the particle, does not become a significant problem. In any case, because the absorbent particles of the present invention are already cross-linked the formation of shell barrier is not nearly as likely to occur as with the guar gum absorbent materials disclosed in the Torr U.S. Pat. No. 3,908,889. Accordingly, no particular problem is encountered when dried cross-linked guar gum mass is reduced to a powder.

It has been found, however, that a particularly preferred drying technique is to freeze-dry the thickened mass of the cross-linked guar gum since this allows the absorbent particles to be recovered as a dry porous, flake material. In accordance with this aspect of the present invention a porous, freeze-dried absorbent cross-linked guar gum material is obtained by dispersing guar gum or a derivative thereof in an aqueous medium to obtain a viscous solution of hydrated guar gum; mixing the viscous solution under high shear conditions until the solution is uniformly homogenized; adding borax or other borate releasing compound to the homogenized solution of hydrated guar gum while stirring the solution until the hydrated guar gum is cross-linked and forms a thickened gellike mass; forming a sheet from the thickened mass freezing the mass, granulating and then freeze-drying the granulated material.

After cross-linking is completed, typically the thickened gelled mass is placed into a tray to form a sheet having a thickness on the order of from about 10 mm to about 3 cm, preferably from about 10 mm to about 1 cm. The sheet is forzen, granulated and then dried by any conventional freezedrying apparatus. Typical parameters for the freeze-drying include a condenser temperature on the order of from about $-100°$ F. to about $-50°$ F., preferably from about $-75°$ F. to about $-50°$ F., a vacuum on the order of from about 10 micrometers Hg to about 500 micrometers Hg, preferably from about 10 to about 50 micrometers Hg; and a shelf heat or sublimation temperature on the order of from about 50° F. to about 150° F., preferably from about 90° F. to about 130° F. A porous, snowwhite, freeze-dried form of absorbent material is obtained. The porous material has a bulk density of about 0.01 gm/cu$^3$ or less, preferably from about 0.005 gm/cm$^3$ to about 0.1 gm/cm$^3$.

The dried borax cross-linked guar gum absorbent product of the invention is odorless and non-toxic and, whether in the form of powder, flake or freeze-dried porous material is readily free-flowing. Upon rehydration with water, urine or other body fluid or aqueous liquid it can firmly hold or absorb up to about 100 times its weight of the liquid and, at a minimum, will be able to hold or absorb, without application of external pressure to the absorbing system, at least an amount of liquid equivalent to the amount of hydration water used to prepare the hydrated guar gum in the initial step of the process. Thus, the dry absorbent particles of the invention can hold up to 100 times their weight in water without becoming sticky and remaining as a coherent mass although a slight amount of flow can be observed. At amounts of absorbed liquid in the range of from about 30 to about 50 times the weight of the dried absorbent particles a thicker non-flowable and relatively dry mass is obtained. The borax cross-linked guar gum absorbent material of the invention exhibits its full absorbing capacity over a very broad temperature range which would encompass at least those temperatures which would be encountered under normal usage conditions. The absorbent material of the invention is also insensitive to saline solutions and other salts which may be encountered in many typical applications such in absorbing urine when used in a diaper, absorbing blood or other drainage from wounds when used in a bandage, for absorbing perspiration when used in gloves or similar apparel or sporting goods, and the like.

The dried borax cross-linked guar gum absorbent product can be used as the absorbent material or as part of the absorbent material by replacing part or all of the absorbent material used in conventional absorbent articles, especially disposable absorbent articles such as disposable diapers, sanitary napkins, tampons, bandages, sporting goods, for example head and wrist sweat bands, gloves and glove linings and the like all of which are used for absorbing and firmly holding body fluids such as urine, blood, perspiration, wound exudates, and the like. For example, when used as the absorbent core or as part of the absorbent core of a conventional box-pleated disposable diaper such as the type described in U.S. Pat. No. 3,893,460 to Karami, the disclosure of which is incorporated herein by reference, the absorbent particles of the invention can merely be sprinkled or dispersed on or throughout the absorbent core of the diaper or other absorbent article. Furthermore, the distribution of the absorbent borax cross-linked guar gum particles on or throughout the absorbent core can be uniform or random or according to a predetermined pattern such as straight or wavy or intersecting lines or a series of dots, lines, etc.

It is also within the scope of the invention to use the absorbent borax cross-linked guar gum as a continuous film to replace or in addition to the absorbent core of the absorbent article.

In its broadest aspect the absorbent products of the present invention include the dried borax cross-linked guar gum particles in the form of a powder, flakes or porous granules or in the form of a film retained on or distributed throughout a substrate material which is preferably flexible such that the article is capable of being held in contact with an animal body whereby the absorbent particles or film of the dried borox cross-linked guar gum are in fluid flow contact with body fluids exuded by the animal body either directly or after passing through a body-contacting cover or top sheet. For example, a disposable diaper which may be for babies as well as for incontinent adults or a sanitary napkin or the like will usually include a body contacting, liquid permeable top sheet, a liquid impervious bottom sheet and an intermediate layer of or containing the absorbent material. The liquid permeable body contacting top or cover sheet which can, in fact, be used to wrap around the outside edges and under the liquid impervious bottom sheet, can be formed, for example, from woven or unwoven cellulosic fibers or other liquid permeable material having sufficient wet-strength and mechanical strength such that it is capable of resisting breakage or disintegration when in contact with the body fluids or when subjected to stress.

The liquid impervious bottom sheet may be formed from any water insoluble film forming plastic material such as polyethylene, nylon and the like. It will be appreciated, of course, that to the extent any of the materials of the absorbent articles come into contact with the human body or other animal body they must be non-toxic and non-irritating.

The intermediate layer or absorbent core can be formed solely from the dried borax cross-linked guar gum particles or film but more preferably the absorbent particles will be simply comingled or distributed throughout a substrate formed from hydrophylic material such as a wood pulp sheet, cellulosic wadding and the like. Cloth fabric, paper, synthetic foam resin or felted fibers may also be used as the support material for the borax cross-linked guar gum particles or film. The amount of the borax cross-linked guar gum absorbent material will depend on, of course, the intended end use of the absorbent article. When used in disposable diapers the amount of the absorbent will be sufficent to hold, without leakage, at least two and preferably five urinations, or about 250 ml. Therefore, the amount of the borax cross-linked guar gum absorbent will range from about 1 gram to about 10 grams, preferably from about 2 to about 5 grams in the absorbent disposable diaper.

In addition to the temperature insensitivity and insensitivity to salts which characterize the absorbing capacity of the borax cross-linked guar gum absorbents of the invention the absorbents are further characterized by the capability of absorbing and holding many times its own weight of liquids such as water, urine, blood, perspiration and the like as a firm stable gel which will not lose the absorbed liquid even when subject to the moderate pressure encountered during use such as the weight of a child when used as the absorbing material in a disposable diaper. However, in accordance with a preferred embodiment of the present invention the capability of the absorbent article to resist the expression of absorbed liquids when external pressures are applied is greatly enhanced by utilizing and incorporating the absorbent material with multicellular structures which confine the absorbed fluids, converted to a gelled state by the absorbent material, contained in the cavities of the multicellular structure. Examples of such suitable multicellular structures include, for example, deeply embossed plastic sheets, e.g. KIMCELL, a product of Kimberly-Clark, or open celled plastic foams, e.g. SCOTTFOAM, a reticulated polyurethane foam product of Scott Paper Company. A specific multicellular (bubble-type) structure as utilized in a disposable diaper with which the borax cross-linked guar gum absorbent of the present invention can be effectively utilized is disclosed in U.S. Pat. No. 4,055,180, the disclosure of which is incorporated herein by reference.

In regard to the use of the multicellular supporting structure it is noted that external forces will be communicated to the supporting structure rather than the confined gel and therefore the absorbed fluid or gel will not be expressed by the external forces.

In using the multicellular supporting structure the dried cross-linked absorbent particles can be directly loaded into the cells or the cells may be impregnated with the hydrated cross-linked gel and dried in situ by any of the procedures discussed above, particularly by freeze-drying.

The following non-limiting examples are presented to further describe the present invention.

EXAMPLE 1

Twenty (20) grams of guar gum (Celanese CMHP a carboxylated hydroxypropylated guar gum derivative) is dispersed in 2 liters of 50° C. water in a steam jacketed vessel equipped with a mechanical stirrer and the mixture is stirred for 30 minutes while adding water to make up for any evaporation at which time the guar gum is fully hydrated.

Independently, an aqueous solution of borax ($Na_2B_4O_7.10H_2O$) is prepared by dissolving about 1 gram borax in 20 ml water. The aqueous borax solution is slowly added to the hydrated guar gum while it is still in the steam heated vessel and thoroughly mixed to form a cross-linked gel.

The cross-linked gel is dried in the same jacketed vessel by steam heat until it is dry. The brittle mass which is recovered can readily be reduced to flake form by manual manipulation.

When 1 part of the dried flakes of the borax cross-linked guar gum in a standard 100 ml Griffen low form beaker is rehydrated at 37° C. with synthetic urine, it is capable of absorbing at least 50 parts of the synthetic urine without becoming flowable, i.e. it remains coherent and will not flow out of the beaker when it is tipped on its side.

EXAMPLE 2

Freeze dried borax cross-linked absorbent porous material is obtained by the following procedure.

Deionized water (8 liters) is heated at 50° C. in a steam jacketed stainless steel reaction vessel equipped with a mechanical stirrer. Eighty (80) grams of the same guar gum as used in Example 1 is dispersed in the water with rapid stirring. The viscous hydrated solution is transferred to a high shear Grifford-Wood mixer where it is thoroughly homogenized in about 30 minutes. An aqueous solution of borax (8 grams borax dissolved in 300 ml water) is then quickly added, with stirring continued, to the homogenized solution. The gelled cross-linked material having a viscosity of about 150,000 centipoises is aged overnight and then placed in a tray to form a sheet having a thickness of about 1 centimeter.

Drying is carried out by a conventional freeze drying apparatus using a vacuum shelf dryer chamber equipped with heating and cooling coils. The chamber is maintained at about 100 micrometers Hg or less. The sheet is frozen to −50° F. The shelf temperature is maintained at about 100° F. for about 2 days. The resulting material is a porous, snow-white, freeze-dried sheet having a density of about 0.01 gm/cm$^3$.

One (1) gram of the porous freeze-dried absorbent material in crushed form is placed loosely in a 100 ml Griffen beaker so that the volume occupied is about 50 ml. The material rapidly absorbs 50 ml of synthetic urine (at 37° C.) and forms a firm gel. The rehydrated mass could still absorb an additional 50 ml without noticeable run-off or leakage. The gel is stable even after several days.

EXAMPLE 3

This Example demonstrates the use of the borax cross-linked guar gum particles in a diaper structure utilizing a multi-cellular bubble sheet for holding the absorbent material.

Into each cell of a 10 cm×10 cm square piece of KIMCELL (a converted polyethylene sheet which is deeply embossed into the form of a honeycomb, i.e. hexagonal close-packed cells, a product of Kimberly-Clark) is placed a small amount (about 4 mg) of the dried sheet obtained in Example 1 in flake form. A total of 320 mg of the borax cross-linked guar gum is used.

Synthetic urine is then added until a total of 19 gm of synthetic urine is entrapped by the 320 mg of absorbent and a firm gel is formed. The stability of the gel is determined by a standard diaper dryness test as follows:

A standard diaper topsheet is placed over the KIMCELL SHEET. A piece of filter paper is then placed over the diaper topsheet under a retaining pressure of 0.5 psi and the whole is inverted. The weight of water picked up by the peice of filter paper, which is a measure of rewetting, is only a trace, about 1 gm.

EXAMPLE 4

In this Example, a hydrated borax cross-linked guar gum prepared in the same manner as in Example 2 is placed in the cells of a KIMCELL sheet an after aging for several hours is freeze-dried by the same procedure used in Example 2. The resulting material with which each cell is filled with the porous absorbed borated guar gum, is capable of absorbing and retaining more than 60 times the weight of absorbent of the synthetic urine.

EXAMPLE 5

Twenty (20) grams of modified guar gum (Celanese CMHP) is slowly added to 1000 ml of 50° F. deionized water with rapid mixing for about 30 minutes to obtain a good dispersion. The temperature is then raised to 120° F. to complete hydration. An aqueous borax solution (2 gm borax in 20 ml deionized water) which has previously been prepared is added to the hydrated guar gum and rapidly stirred for 10 minutes during which time the gel forms. The gelled cross-linked mass is transferred into a beaker and allowed to set and cool in the air. The mass is spread out and permitted to dry in air at room temperature, the dried absorbent taken from the beaker is capable of absorbing and holding over 50 times its weight of water while remaining as a fairly firm gel.

EXAMPLE 6

Twenty (20) grams of guar gum as in Example 1 is hydrated as in that Example (paragraph 1) using 2 liters of 50° C. water. The resultant dispersion is used to impregnate a polyurethane sponge 15 cm×25 cm×10 cm thick) to a pickup of 200% based on the weight of the sponge. The impregnated sponge is then further treated with an aqueous borax solution (2 g. in 20 ml deionized water). The product is then freeze dried as in Example 2.

EXAMPLE 7

Examples 2, 2, 3, 5 and 6 are repeated using the following:
(1) polyvinyl alcohol
(2) gum arabic
(3) gum acacia
(4) galactose
(5) pectin

EXAMPLE 8

This Example demonstrates the ability of borax cross-linked guar gum to hydrate and gel acidic solutions (e.g. urine) when used as a blend with alkaline materials.

Freeze dried borax cross-linked absorbent material as prepared in Example 2 is mixed with an alkaline material (e.g. Na$_5$P$_3$O$_{10}$, M$_{90}$). The alkaline material is present in sufficient quantity to neutralize acids in solutions such as human urine. This mixture can absorb more than 50 times its weight in urine.

While the present invention has been described generally with regard to guar gum, it is manifestly clear that other equivalent, i.e. cis-1,2-diol polysaccharide materials (as in Example 7) can be used as well. Such materials are well-known and include locust bean gum, gum arabic, gum acacia, algins, pectins and hemi-celluloses which contain cis-1,2-diols such as rhamrose, mannose and galactose. In addition, uniquely, polyvinyl alcohol including partially hydrolyzed poly vinyl acetate, can also function similarly as the aforementioned cis-1,2-diols.

What is claimed is:
1. A process for preparing an absorbent material in dry form which comprises:mixing a cis-1,2-diol containing polysaccharide material with water in amount and for time sufficient to at least substantially completely hydrate the material; adding an aqueous solution of a source of borate ions to the hydrated material to crosslink same and form a thickened gelled mass; and dehydrating the thickened mass to drive off water contained therein, said polysaccharide being guar gum, said thickened mass being dehydrated by freeze drying.

2. The process of claim 1, wherein the amount of water used to hydrate the cis-1,2-diol is from about 30 parts to about 100 parts water per part of same.

3. The process of claim 1, wherein the guar gum is carboxymethylated hydroxypropylated guar gum.

4. The process of claim 1, wherein the thickened mass is dehydrated to a water content of from about 0% to about 20%.

5. The process for obtaining a porous, freeze-dried absorbent material which comprises the steps of:
dispersing a cis-1,2-diol polysaccharide material in an aqueous medium to obtain a viscous solution of hydrated polysaccharide;
mixing the viscous solution under high shear conditions until the solution is uniformly homogenized;
then adding borax or other borate ion releasing compound to the homogenized solution of hydrated polysaccharide while stirring the solution to crosslink the hydrated polysaccharide and form a thickened gelled mass;
placing the thickened gelled mass on a substrate; and
freeze-drying said thickened gelled mass to obtain a porous freeze-dried absorbent cross-linked polysaccharide material.

6. The process of claim 5 wherein the freeze-drying is performed by utilizing a condenser temperature of from about $-50°$ F. to $-150°$ F., a vacuum of from about 10 to about 500 microns of mercury and a shelf temperature of about 50° F. to about 150° F.

7. The process of claim 5 wherein the substrate is multi-cellular substrate.

8. The process of claim 7 wherein the multicellular substrate is an embossed plastic sheet, wherein the thickened gelled mass is deposited in the embossed cells.

9. The process of claim 7 wherein the multicellular substrate is an open celled plastic foam wherein the thickened gelled mass is impregnated into the open cells.

* * * * *